(12) United States Patent
Gubbels et al.

(10) Patent No.: US 8,586,690 B2
(45) Date of Patent: Nov. 19, 2013

(54) PROCESS FOR THE PRODUCTION OF POLYSILALKYLENESILOXANES

(75) Inventors: Frederic Gubbels, Houtain-le-Val (BE); Stephanie Lobry, Rombies et Marchipont (FR); Francois Ganachaud, Decines (FR); Amedee Ratsimihety, Montpellier (FR)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/505,716

(22) PCT Filed: Nov. 2, 2010

(86) PCT No.: PCT/EP2010/066661
§ 371 (c)(1),
(2), (4) Date: May 2, 2012

(87) PCT Pub. No.: WO2011/054830
PCT Pub. Date: May 12, 2011

(65) Prior Publication Data
US 2012/0226010 A1  Sep. 6, 2012

(30) Foreign Application Priority Data
Nov. 3, 2009  (EP) ..................... 09306051

(51) Int. Cl.
*C08G 77/06* (2006.01)
*C08G 77/60* (2006.01)

(52) U.S. Cl.
USPC .................... 528/37; 528/12; 528/23; 528/35

(58) Field of Classification Search
None
See application file for complete search history.

(56) References Cited

U.S. PATENT DOCUMENTS

| | | | |
|---|---|---|---|
| 3,839,388 A | 10/1974 | Nitzsche et al. | |
| 4,564,693 A | 1/1986 | Riederer | |
| 4,701,490 A | 10/1987 | Burkhardt et al. | |
| 5,087,720 A * | 2/1992 | Kishita et al. | 556/434 |
| 5,117,025 A | 5/1992 | Takago et al. | |
| 5,442,083 A | 8/1995 | Kobayashi | |
| 6,080,829 A | 6/2000 | Tapsak et al. | |
| 6,492,480 B1 * | 12/2002 | Nagashima et al. | 528/19 |
| 6,534,587 B1 | 3/2003 | Tapsak et al. | |

FOREIGN PATENT DOCUMENTS

| | | | |
|---|---|---|---|
| EP | 0215470 A2 | 3/1987 | |
| EP | 0860461 A2 | 8/1998 | |
| EP | 1008598 A2 | 6/2000 | |
| GB | 2252975 A | 8/1992 | |
| WO | WO 99/67319 A1 | 12/1999 | |

OTHER PUBLICATIONS

English language abstract for EP 0215470 extracted from the espacenet.com database on Jun. 21, 2012, 15 pages.
Schwesinger et al., "Extremely Strong, Uncharged Auxiliary Bases; Monomeric and Polymer-Supported Polyaminophosphazenes (P2-P5)", Liebigs Ann. 1996, pp. 1055-1081.
International Search Report for Application No. PCT/EP2010/066661 dated Feb. 11, 2011, 4 pages.
L.V. Interrante et al., "Synthesis and Studies of Polymers Having a Regular [Si-C-Si-O]n Backbone Structure: The Poly(Silylenemethylene-co-Siloxanes)", Chemistry Department, Rensselaer Polytechnic Institute, Polymer Preprints 2001, 41(1), pp. 225-226.
L. V. Interrante et al., "Poly(dimethylsilylenemethylene-co-dimethysiloxane): A Regularly Alternating Copolymer of Poly (dimethylsiloxane) and Poly(dimethylsilylenemethylene)", American Chemical Society, Macromolecules 2001, 34, pp. 1545-1547.
T. Kh. Islamov et al., "Cleavage of Cyclocarbosiloxanes in the Presence of Nucleophilic Catalysts", Bulletin of the Academy of Sciences of the USSR, Division of Chemical Sciences, No. 12, 1969, pp. 2573-2578.
Mark A. ATapsak et al., "Preparation of Cyclosilalkylenesiloxane Monomers and Their Cationic ROP", Journal of Inorganic and Organometallic Polymers, vol. 9, No. 1, 1999, pp. 35-53.

\* cited by examiner

*Primary Examiner* — Marc Zimmer
(74) *Attorney, Agent, or Firm* — Howard & Howard Attorneys PLLC

(57) ABSTRACT

The present invention relates to a process for the production of an intermediate siloxane monomer and use of said monomer to produce high molecular weight linear polysilalkylenesiloxanes. The siloxane monomer is prepared by ring opening polymerization of a cyclic monomer of the structure in the presence of an acidic or basic ring opening polymerization catalyst; to form a mixture of siloxane monomers and linear oligomers. The linear oligomers are then extracted and discarded before a further step of ring opening polymerization using the aforementioned intermediate siloxane monomer mixture as the starting material. The second polymerization step is undertaken at a temperature within the melting point range of said siloxane monomer mixture. The intermediate, final product and methods of their manufacture are described.

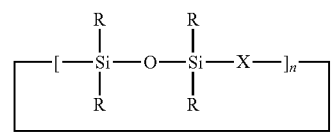

19 Claims, 1 Drawing Sheet

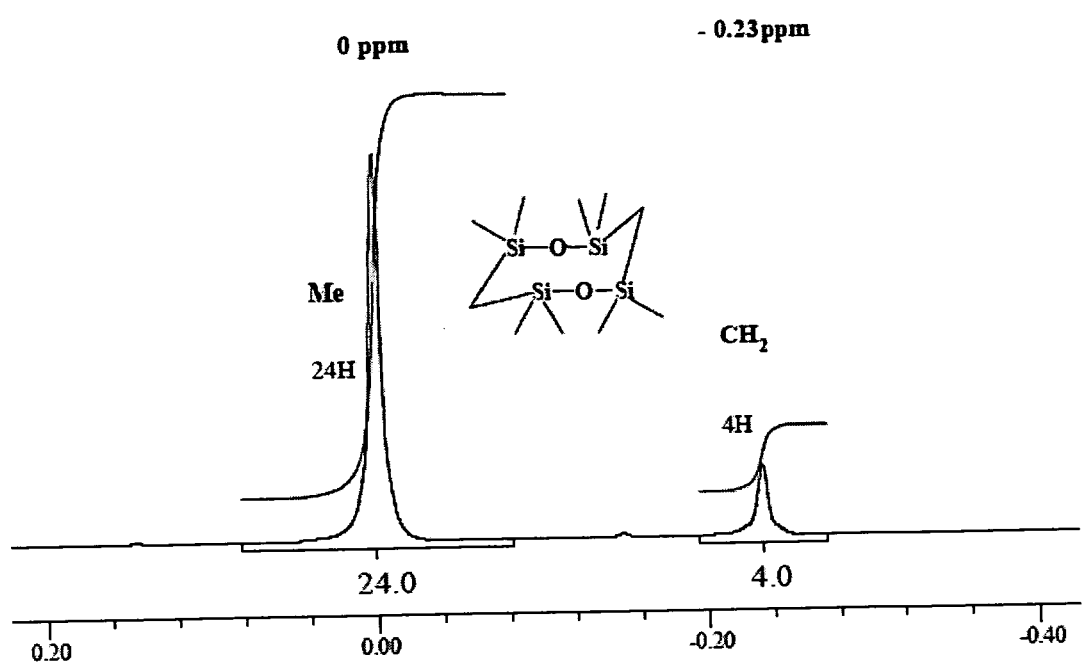

PROCESS FOR THE PRODUCTION OF POLYSILALKYLENESILOXANES

RELATED APPLICATIONS

This application claims priority to and all the advantages of International Patent Application No. PCT/EP2010/066661, filed on Nov. 2, 2010, which claims priority to European Patent Application No. EP09306051.5, filed on Nov. 3, 2009.

The present invention relates to a process for the production of a siloxane monomer mixture and use of said siloxane monomer mixture to produce high molecular weight linear polysilalkylenesiloxanes.

Polysilalkylenesiloxanes are less susceptible to molecular chain scission by ionic substances than pure siloxanes and are therefore sought after for use in applications where thermal and chemical stability is required. However, these polymers/copolymers are difficult and/or expensive to prepare. A variety of chemical processes for the preparation of polysilalkylenesiloxanes have been identified for their manufacture but a general failing of these current processes is that they are unable to provide long chain polymers. Examples of processes previously proposed include the following:

U.S. Pat. No. 5,117,025 describes a process for the ring opening polymerization of cyclic silethylenesiloxane. The products obtained have an average molecular weight of up to about 50,000. The procedure describes the use of a monomer which is difficult to synthesize and requires stringent experimental conditions both of which limit commercial interest in this technique.

For the sake of clarification, ring-opening polymerisation with respect to siloxane chemistry relates to a polymerisation process using cyclosiloxane based starting materials. The cyclosiloxane based starting materials undergo a polymerisation process involving the ring opening of the cyclosiloxanes by reaction in the presence of a "ring opening polymerisation" catalyst such as an acid or base. An equilibrium between the desired resulting high-molecular compounds and a mixture of cyclic compounds and/or linear oligomers is set up in the course of the polymerisation reaction. The resulting equilibrium largely depends on the nature and amount of siloxane(s), the catalyst used and on the reaction temperature. Such polymerisation processes are generally carried out in the absence of a solvent, but in the past have been prepared in solvents (e.g. polar and non-polar organic solvents) or in emulsion. However, the use of solvents and/or emulsions are not recommended due to the need for complex processes for their removal after the reaction is complete.

U.S. Pat. No. 5,442,083 describes a hydrosilylation polymerization process between an Si—H terminated organosiloxane and an unsaturated aliphatic hydrocarbon that contains 2 carbon-carbon double bonds or one carbon-carbon double bond and one carbon-carbon triple bond as an alternate route. A method to produce such polymers using silylhydrogen functional intermediates as an alternative to ring opening polymerization of cyclic silethylenesiloxane is described. However, the molecular weight of the resulting products is rather limited (<10,000). The authors of U.S. Pat. No. 5,442,083 indicate that ring opening polymerization routes are not preferred because they partially depolymerise resulting in reduced yields of the silalkylenesiloxane copolymer.

Hydrosilylation step growth polymerization as a method of silalkylenesiloxane copolymer synthesis also contains inherent disadvantages. In order to produce high degree of polymerisation (DP) copolymers, the stoichiometry of the Si—H and unsaturated hydrocarbon moieties must be as close to 1:1 as possible. Side reactions which disturb this balance limit the DP of the copolymer by creating terminating groups on unsaturated hydrocarbon monomers and rendering the monomers less susceptible to hydrosilylation.

WO 99/67319 discloses a procedure to obtain high molecular weight silalkylene by ring opening polymerization. However, the number of carbon in the alkyl chain is at least 6.

Interrante et al describe a method of ring opening polymerization of 1,1,3,3,5,5,7,7-Octamethyl-2,6-dioxa-1,3,5,7-tetrasilacyclooctane to produce poly(dimethylsilylenemethylene-co-dimethylsiloxane. Triflic acid (trifluoromethane sulfonic acid) is used at room temperature to produce an alternate silmethylene siloxane polymer by ring opening polymerization with a reasonable yield [Polym. Preprints 2001, 42(1), 225]. However, the process taught by Interrante et al. actually appears to produce a high proportion of macrocyclic molecules which aren't suitable for the production of high molecular weight linear polymers sought herein. Interrante et al. were only able to produce polymers with moderate molecular weights up to 30,000.

U.S. Pat. No. 6,080,829 describes a method to produce cyclic monomers that can be used for the synthesis of the starting molecule used herein. Moreover, in Journal of Inorganic and Organometallic Polymers 1999, 9(1), 35-53, Tapsak and al. further describe a method to produce high molecular weight Silalkylenesiloxane containing linear alkyl chains having from 6 to 14 carbon atoms by cationic ring opening polymerization using an ion-exchange resin with good yield. U.S. Pat. No. 6,534,587B1 describes a method to produce copolymers of silakylenesiloxane and siloxanes using the above mentioned technique developed by Tapsak.

A new process has been identified for the production of an activated siloxane monomer and subsequently high molecular weight (>100,000 g/mol) linear polysilalkylenesiloxanes.

In accordance with the present invention there is provided a siloxane monomer mixture obtainable by a process comprising the steps of a) ring opening polymerization of a cyclic monomer of the structure

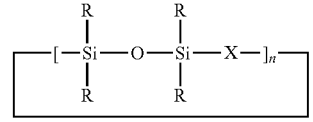

Where X is selected from
(i) a linear or branched alkylene group having from 1 to 14 carbon atoms; and
(ii) an aromatic group having from 6 to 20 carbon atoms;
each R is the same or different and is selected from H, OH, a hydrocarbon group having from 1 to 18 carbon atoms, a substituted hydrocarbon group having from 1 to 18 carbon atoms or a hydrocarbonoxy group having up to 18 carbon atoms and n is an integer between 1 and 6, in the presence of an acidic or basic ring opening polymerisation catalyst to form a mixture of siloxane monomers and linear oligomers b) removing the linear oligomers prepared in step (a) optionally using a suitable solvent; and c) removing the aforementioned solvent, when present.

The process steps are sequential.

In accordance with a second embodiment of the invention there is provided a method for obtaining a siloxane monomer mixture comprising the steps of a) ring opening polymerization of a cyclic monomer of the structure

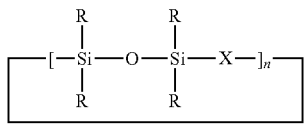

Where X is selected from (i) a linear or branched alkylene group having from 1 to 14 carbon atoms and which optionally may contain substituted groups; and (ii) an aromatic group having from 6 to 20 carbon atoms;

each R is the same or different and is selected from H, OH, a hydrocarbon group having from 1 to 18 carbon atoms, a substituted hydrocarbon group having from 1 to 18 carbon atoms or a hydrocarbonoxy group having up to 18 carbon atoms and n is an integer between 1 and 6, in the presence of an acidic or basic ring opening polymerisation catalyst, to form a mixture of siloxane monomers and linear oligomers;

b) removing the linear oligomers prepared in step (a) optionally using a suitable solvent; and c) removing the aforementioned solvent, when present.

The "linear oligomers" described above, which are extracted at the end of the ring opening polymerisation reaction, are macrosiloxanes of moderate molecular weight (e.g. a molecular weight of from 20,000 to 45,000 g/mol as measured by Triple Detection Size Exclusion Chromatography and calculated on the basis of polystyrene molecular weight standards). At completion of the ring opening polymerisation reaction these linear oligomers are in equilibrium with the mixture of siloxane monomers (containing a significant proportion of the cyclic monomer starting material and derivatives thereof). However, in the present case it is the linear oligomers which are separated and discarded and the resulting siloxane monomer mixture which is retained and, if appropriate, purified prior to being used in a second ring opening polymerisation reaction as discussed below. These linear oligomers or macrosiloxanes would usually be collected as the end product of such ring opening polymer but it has been identified that products of significantly higher molecular weight may be obtained as described herein by the removal of the linear oligomers and the use of the remaining siloxane monomer mixture in a second ring opening polymerisation reaction.

In a further embodiment of the present invention there is provided a use for the siloxane monomer mixture resulting from the above described process in the preparation of high molecular weight linear polysilalkylenesiloxanes comprising the following repeating units

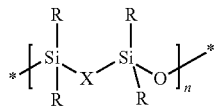

wherein X, R and n are as hereinbefore described.

The cyclic monomer used in accordance with the present invention has the general structure

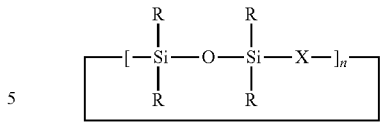

Each X may be the same or different and is selected from (i) a linear or branched alkylene group having from 1 to 14 carbon atoms; and (ii) an aromatic group having from 6 to 20 carbon atoms.

Alternatively each X is a linear or branched alkylene group having from 1 to 6 carbon atoms. Typically X is a methylene group or an ethylene group. The linear or branched alkylene group may contain a degree of substitution.

For the purpose of this application "Substituted" means one or more hydrogen atoms in a hydrocarbon group has been replaced with another substituent. Examples of such substituents include, halogen atoms such as chlorine, fluorine, bromine, and iodine; halogen atom containing groups such as chloromethyl, perfluorobutyl, trifluoroethyl, and nonafluorohexyl; oxygen atoms; oxygen atom containing groups such as (meth)acrylic, carboxyl and polyethers; nitrogen atoms; nitrogen atom containing groups such as amino-functional groups, amido-functional groups, and cyano-functional groups; sulphur atoms; and sulphur atom containing groups such as mercapto groups.

Each R in the cyclic monomer may be the same or different and is selected from H, OH, a hydrocarbon group having from 1 to 18 carbon atoms, a substituted hydrocarbon group having from 1 to 18 carbon atoms or a hydrocarbonoxy group having up to 18 carbon atoms. Alternatively R is an, optionally substituted, alkyl or alkenyl, group having up to 8 carbon atoms. The optionally substituted alkyl group can be, for example, methyl, ethyl, n-propyl, trifluoropropyl, n-butyl, sec-butyl, and tert-butyl. The alkenyl group can be, for example, vinyl, allyl, propenyl, and butenyl. As a further alternative R may comprise an aryl, alkaryl or aralkyl group having from 6 to 12 carbon atoms. The aryl and aralkyl groups can be, for example, phenyl, tolyl, and benzoyl. The substituted groups may be as defined above. Preferred R groups are alkyl groups having from 1 to 6 carbon atoms, typically methyl and/or ethyl groups.

The value of n is from 1 to 6. Alternatively the value of n is between 2 and 6 but it is preferred that n has a value of 2, 3 or 4.

A specific example of cyclic monomer is 1,1,3,3,5,5,7,7-Octamethyl-2,6-dioxa-1,3,5,7-tetrasilacyclooctane, where X is a methylene group, each R is a methyl group and n is 2.

The ring opening polymerisation catalyst used in step (a) of the process may comprise one or more suitable basic catalysts. These include alkali metal hydroxides such as lithium hydroxide, sodium hydroxide, potassium hydroxide, rubidium hydroxide or cesium hydroxide, alkali metal alkoxides or complexes of alkali metal hydroxides and an alcohol, alkali metal silanolates such as potassium silanolate, rubidium silanolate, cesium silanolate, sodium silanolate and lithium silanolate or trimethylpotassium silanolate. Other basic ring opening polymerisation catalysts which might be utilised include the catalysts which are the products resulting from the reaction of a tetra-alkyl ammonium hydroxide and a siloxane tetramer. These various catalyzing agents have different relative reactivities with respect to the present polymerization process, and accordingly, compensation must be made for them. For example, sodium hydroxide will catalyze the reaction more slowly than the others, and therefore the reaction takes longer at any given temperature. On the other hand, cesium hydroxide causes reaction to take place more rapidly. Thus cesium hydroxide may be more effective when a lower reaction temperature is employed or when it is desired to produce a silicone gum having a very high viscosity. Of the above potassium silanolate is particularly preferred as it is an active form of potassium hydroxide and which is also very soluble in a monomer solution such as octamethylcyclotetrasiloxane. The catalyst concentration can be from about 5 ppm to about 500 ppm of Equivalent KOH. The KOH equivalence of potassium silanolate ranges from approximately 0.05% to 6.0% KOH by weight. In the preferred embodiment of the process of the present invention potassium silanolate is employed at a KOH concentration of about 20 ppm by weight.

The ring opening polymerisation catalyst used in step (a) of the process may comprise one or more suitable acidic catalysts. Any suitable acidic ring opening polymerisation catalyst may be utilized as the catalyst. A mixture of such catalysts may alternatively be used. These include acid solutions, for example, solutions comprising acetic acid, formic acid, propionic acid, glycolic acid, valeric acid, butyric acid, caproic acid, caprylic acid, capric acid, octanoic acid, lauric acid, myristic acid, stearic acid, palmitic acid, oleic acid, undecylenic acid, Lewis acids, such as $BF_3$, $AlCl_3$, t-BuCl/$Et_2AlCl$, $Cl_2/BCl_3$, $AlBr_3$, $AlBr_3.TiCl_4$, $I_2$, $SnCl_4$, $WCl_6$, $AlEt_2Cl$, $PF_5$, $VCl_4$, $AlEtCl_2$, $BF_3Et_2O$, $PCl_5$, $PCl_3$, $POCl_3$, $TiCl_6$, $SbCl_5$, $(C_6H_5)_3C+(SbCl_6)-$, acrylic acids, polyacrylic acids, polymethacrylic acids, functionalized organohalosilanes, functionalized organohalosilanes combined with a disilazane, dimethylvinylsilyl acetate or phosphorus-based compounds, such as phosphorus pentoxide, trichloroethyl phosphite, tris(methylsilyl) phosphate and phosphoric acid, phosphonitrile halide catalysts (sometimes referred to as acidic phosphazenes) and phosphazene bases (such as those described in EP 0860461 and EP 1008598 the content of which are included herein by reference) may be used. A solution based on dry ice can also be envisaged for the acid solution. Strong protonic acids, in particular heteropoly acids, perchloric acid, sulfuric acid, hydrochloric acid, HI, HBr, $HClO_4$, $H_2SO_4$, $HNO_3$, $H_3PO_4$, para-toluenesulfonic acid, trifluoroacetic acid, perfluoroalkenesulfonic acids such as trifluoromethanesulfonic (triflic) acid or esters or salt of strong acids such as Methyl tosylate, methyl triflate and silyl ester trifluoromethane sulfonic acid are preferred catalysts. A particularly suitable catalyst for this process is triflic acid.

Preferred phosphonitrile chloride, catalysts include those prepared according to U.S. patent specifications U.S. Pat. Nos. 3,839,388 and 4,564,693 or EP application 215 470 and phosphonitrile halide ion based catalysts, as described in GB2252975, having the general formula $[X^2(PX^2_2=N)_s PX^2_3]^+[M^2X^2_{(v-t+1)}R^{III}_t]^-$, wherein $X^2$ denotes a halogen atom, $M^2$ is an element having an electronegativity of from 1.0 to 2.0 according to Pauling's scale, $R^{III}$ is an alkyl group having up to 12 carbon atoms, s has a value of from 1 to 6, v is the valence or oxidation state of $M^2$ and t has a value of from 0 to v−1.

Further alternative catalysts suitable for use in the present invention may comprise oxygen-containing chlorophosphazenes containing organosilicon radicals having the following general formula:

$$Z^1\text{—}PCl_2\text{=}N(\text{—}PCl_2\text{=}N)_n\text{—}PCl_2\text{—}O$$

in which $Z^1$ represents an organosilicon radical bonded to phosphorus via oxygen, a chlorine atom or the hydroxyl group and n represents 0 or an integer from 1 to 8. The catalyst may also comprise condensation products of the above and/or tautomers thereof (the catalyst exists in a tautomeric form when $Z^1$ is a hydroxyl group). All or some of the chlorine atoms can be replaced by radicals Q, in which Q represents the hydroxyl group, monovalent organic radicals, such as alkoxy radicals or aryloxy radicals, halogen atoms other than chlorine, organosilicon radicals and phosphorus-containing radicals. The oxygen-containing chlorophosphazenes of formula (I) are preferably those in which no chlorine atom is replaced by a radical Q. Numerous phosphazene bases and routes for their synthesis have been described in the literature, for example in Schwesinger et al, Liebigs Ann. 1996, 1055-1081.

The reaction in step (a) may be carried out at any suitable temperature. Temperatures between 15° C. and 50° C. are preferred. Optionally an inert atmosphere can be used to carry out the reaction.

Any suitable separation process may be utilized to remove (extract) the oligomeric by-product (i.e. the linear oligomers) at the end of step (a). One suitable separation process identified is the introduction of a solvent into the mixture collected at the end of step (a) to precipitate out the oligomer, which can then be easily extracted by filtration or the like, with the solvent added being subsequently removed to leave the siloxane monomer mixture. Other separation processes which may be utilised include but are not limited to solvent extraction, size exclusion, ion exchange or liquid chromatography.

As previously discussed it has been identified that the aforementioned siloxane monomer mixture has been found to surprisingly produce high molecular weight linear polysilalkylenesiloxanes. The high molecular weight linear polysilalkylenesiloxanes are typically prepared by subjecting the siloxane monomer mixture to ring opening polymerisation, preferably in the presence of the same catalyst involved in the preparation of the siloxane monomer mixture. Alternative catalysts or mixtures thereof may be utilized but are not preferred. A particularly suitable catalyst for this process is, for example, triflic acid.

In a fourth embodiment of the present invention there is provided a process for obtaining a polysilalkylenesiloxane polymer comprising the following repeating units

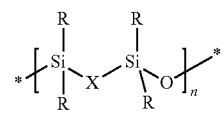

Where X, R and n are as herein before described
which process comprises the steps of reacting the aforementioned siloxane monomer mixture, in the presence of the same acidic or basic ring opening polymerisation catalyst as previously mentioned, at a temperature within the melting point range of said mixture.

In a still further embodiment of the present invention there is provided a process for obtaining a high molecular weight polysilalkylenesiloxane polymer comprising the following repeating units

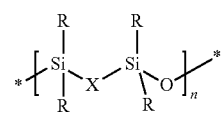

Where X, R and n are as hereinbefore described
comprising the steps of
a) ring opening polymerization of a cyclic monomer of the structure

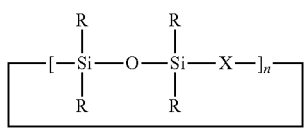

Where X and R are as hereinbefore described, and n is an integer between 1 and 6, in the presence of an acidic or basic ring opening polymerisation catalyst; to form a mixture of siloxane monomers and linear oligomers
b) removing the linear oligomers prepared in step (a) optionally using a suitable solvent; and
c) removing the aforementioned solvent, when present to prepare a siloxane monomer mixture; then,
d) ring opening polymerizing the aforementioned siloxane monomer mixture, in the presence of the same acidic or basic ring opening polymerisation catalyst as previously mentioned, at a temperature within the melting point range of said siloxane monomer mixture.

It is surprising that this 2 step process results in the production of polymers of significantly greater molecular weight than the linear oligomers produced in the first ring opening polymerisation reaction. For the avoidance of doubt high molecular weight linear polysilalkylenesiloxanes for as described herein is intended to mean polysilalkylenesiloxanes with a number average molecular weight (Mn) of greater than 100 000 (g/Mol) as measured by Triple Detection Size Exclusion Chromatography and calculated on the basis of polystyrene molecular weight standards.

It has been identified that perhaps most surprising of all is the fact that this second ring opening polymerisation step only appears to produce the required high molecular weight linear polysilalkylenesiloxanes when the ring opening polymerisation reaction is undergone at a temperature within the melting point range of said siloxane monomer mixture. It will be appreciated that whilst pure compounds can have an absolute value as a melting point mixtures melt over a temperature range which can be as much as 10 or 15° C. Hence, in the case when triflic acid is used as the catalyst in both step (a) and in the ring opening polymerisation to produce high molecular weight linear polysilalkylenesiloxanes from cyclic monomer 1,1,3,3,5,5,7,7-Octamethyl-2,6-dioxa-1,3,5,7-tetrasilacyclooctane, the ring opening polymerisation of the siloxane monomer mixture can take place within a temperature of from about 17° C. to 30° C.

The invention will now be described by way of Example.

EXAMPLES

Whilst the present application covers a wide selection of starting materials the following examples use (for the sake of example only) of 1,1,3,3,5,5,7,7-Octamethyl-2,6-dioxa-1,3,5,7-tetrasilacyclooctane as the cyclic monomer. Throughout the following examples and comparative examples, the molecular weight measurements Mn, cyclic dimer (1,1,3,3,5,5,7,7-Octamethyl-2,6-dioxa-1,3,5,7-tetrasilacyclooctane) content and linearity of the polymer were determined by triple detection size exclusion chromatography in tetrahydrofuran solvent (sometimes alternatively referred to as GPC (i.e. gel permeation chromatography). A TDA 300-EXD apparatus from Viscotek Corporation was utilised to measure Light scattering, viscosimetry and refractive index as a means of determining Mark Houwink parameters and thereby linearity of the polymer. Samples tested had a concentration of 10 mg ml$^{-1}$, and were injection into the system 100 µl. Polymer glass temperature (Tg) was determined using differential scanning calorimetry (scanning temperature from −150° C. to 100° C. in 20° C./min, using a PERKIN ELMER Pyris 1 apparatus calibrated with indium and n-octane.

Preparation of Cyclic Monomer

The cyclic monomer may be prepared via any suitable method of preparation. In the case of 1,1,3,3,5,5,7,7-Octamethyl-2,6-dioxa-1,3,5,7-tetrasilacyclooctane several routes to its preparation have been described and any of these may be used, but for the sake of completion the 2 step method used for its preparation in this series of examples is depicted below.

Synthesis of bis-(chlorodimethylsilyl)-methane 40.4 g (0.2519 mol) [1 mol part] of bis-(trimethylsilyl)-methane (Gelest), 200 g (1.84 mol)[7.3 mol part] of trimethylchlorosilane (Aldrich) and 4 g (0.03 mol) [0.12 mol part] of aluminum chloride (Aldrich) were added in a three-necked round bottom flask and stirred at 57° C. under an argon blanket. Any tetramethyl silane formed was distilled off from the reactor to drive the formation of the bis(chlorosilane). The temperature of the reaction was maintained below 80° C. to prevent the formation of tris-chlorosilane or other isomers throughout the duration of the preparation. After 48 hours, 150 g of trimethylchlorosilane was collected. After cooling, the reaction mixture was evaporated at room temperature and 20 ml of acetone was added into the flask to deactivate the catalyst. The final product was purified by distillation at 63° C. under a reduced pressure of 20 mmHg. A purity of about 95% is obtained with a yield of ca. 80%.

Synthesis of the 1,1,3,3,5,5,7,7-Octamethyl-2,6-dioxa-1,3,5,7-tetrasilacyclooctane Zinc oxide (17.5 g, 0.209 mol) (1.6 mol part) and ethyl acetate (54 ml) were introduced into a 250 ml round-bottom three-necked flask which was equipped with a dropping funnel, a mechanical stirrer, and a reflux condenser with a nitrogen outlet. Over a period of 1 hour, a solution of (27 g, 0.1343 mol) (1 mol part) of bis-(chlorodimethylsilyl)-methane in 40 ml of ethyl acetate, was added at room temperature to the flask. After the addition was complete, stirring was continued for 8 hours. The resulting mixture was then introduced into 83 ml of saturated aqueous sodium bicarbonate solution under vigorous stirring. The organic phase was separated and dried with anhydrous sodium sulfate. The resulting dried product was then purified by distillation at 60° C. under a reduced pressure of 1 mbar. About 15 g of 1,1,3,3,5,5,7,7-Octamethyl-2,6-dioxa-1,3,5,7-tetrasilacyclooctane is obtained, which corresponds to a yield of about 40%. $^1$H NMR (400 Mhz, CDCl$_3$) of the purified product is shown in FIG. 1; δ=0 (s, 24H) SiCH$_3$; −0.23(s, 2H) SiCH$_2$ Comparative Example 1

The process advocated by Interrante et al. was followed in an attempt to produce high molecular weight linear polymers by a series of one step processes for the ring opening polymerization of 1,1,3,3,5,5,7,7-Octamethyl-2,6-dioxa-1,3,5,7-tetrasilacyclooctane using the following process. The polymerization conditions and results are described below in table 1.

In each process 2 g of 1,1,3,3,5,5,7,7-Octamethyl-2,6-dioxa-1,3,5,7-tetrasilacyclooctane obtained as described above and 2 μl of triflic acid were introduced in to a three-necked round bottom flask and stirred under an argon blanket in the conditions indicated below.

TABLE 1

| Reaction Temperature (° C.) | Reaction time (h) | Mn (GPC) (g/mol) | Tg (° C.) | Cyclic dimer content (i.e. starting material where n = 2) (%) | Determination of linearity by triple detection gas permeation chromatography |
|---|---|---|---|---|---|
| 10 | 48 | 1936 | −114 | 65 | Cyclic |
| 25 | 48 | 23300 | NA | 38 | Linear |
| 25 | 72 | 25500 | NA | 38 | Linear |
| 25 | 96 | 30750 | −104 | 38 | Linear |
| 30 | 96 | 9000 | NA | NA | Mixture linear and cyclic |
| Then 25 | 168 | 21400 | | | Linear molecule |
| 40 | 48 | 2000 | −114 | 50 | Cyclic |
| 60 | 48 | 3400 | −111 | 50 | Cyclic |

Subsequent to initiation the molecular weight of the polymer chains was observed to increase in an essentially linear relationship with time throughout the duration of the reaction process, indicating that the polymerization process was relatively slow. It will also be noted that linear oligomers were only prepared when the process took place in a relatively narrow temperature range. Otherwise, it was found to our surprise that the macromolecules formed were mainly macrocyclic molecules. When produced within the narrow temperature range, a yield of about 50% was obtained after 78 hour of polymerization but the average molecular weight was only about 30,000 g/mol. It was found that undertaking the experiment at 30° C. lead to the preparation of a mixture of linear and cyclic molecules but that allow the temperature to drop to back down to about 25° C. resulted in a significant increase in the amount of linear molecules present in the mixture.

Example 1

Preparation of the Siloxane Monomer Mixture 8 g of 1,1,3,3,5,5,7,7-Octamethyl-2,6-dioxa-1,3,5,7-tetrasilacyclooctane (cyclic monomer) obtained as described above and 8 μl of triflic acid were introduced into a three-necked round bottom flask and stirred under argon blanket for 96 h at 25° C. resulting in the preparation of a mixture of siloxane monomers and linear oligomers. Methanol (chromatographic grade) was introduced into the mixture in an amount of 1 volume part of mixture to 10 volume parts of methanol. The linear oligomers present were precipitated out due to the presence of the methanol and then easily separated from the supernatant containing the residual mixture of siloxane monomers. Methanol was removed from the resulting supernatant by evaporation in a rotatory evaporator to yield a crude mixture of siloxane monomers. The siloxane monomers were purified by distilling the crude mixture to yield a 98% yield of the mixture of siloxane monomers. The purified siloxane monomers were then characterized by proton confirming the presence of the siloxane monomer mixture in accordance with the present invention.

Example 2

Preparation of High Molecular Weight Polysilalkylenesiloxane Polymer (Product A)

2 g of product the siloxane monomer mixture, produced in Example 1 and 2 μl of triflic acid were introduced into a three-necked round bottom flask and stirred under argon blanket for 4 h at 25° C. Product A was then collected by precipitated in a mixture of excess methanol and 2 μL of triethylamine.

Example 3

Preparation of High Molecular Weight Polysilalkylenesiloxane Polymer (Product B)

4 g of the siloxane monomer mixture as prepared above and 4 μl of triflic acid in a solvent (dichloromethane) were introduced into a three-necked round bottom flask and stirred under argon blanket for 4 h at 25° C. to produce product B. Product B was precipitated in a mixture of excess methanol and 4 μl triethylamine.

Comparative Example 2

The methanol soluble phase produced in Example 3 was then has been evaporated and purified by distillation to obtain product C, i.e., the unreacted 1,1,3,3,5,5,7,7-Octamethyl-2,6-dioxa-1,3,5,7-tetrasilacyclooctane. 1 g from Example 3, 4 μl of triflic acid was then added, with product C to a three-necked round bottom flask and stirred under argon blanket for 96 h at 25° C. to lead to product D. However, this process failed to produce high molecular weight polymers as will be seen in Table 2 below. It is thought that this may be because the introduction of the triethylamine into the methanol soluble phase in Example 3 effectively neutralized any remaining acidic species therein such as residual triflic acid.

TABLE 2

| Products | Reaction conditions (h)/(° C.) | Mn (GPC) (g/mol) | Tg (° C.) | Cyclic dimer content (i.e. starting material where n = 2) (%) | Determination of linearity by triple detection gas permeation chromatography |
|---|---|---|---|---|---|
| A | 4/25 | 141,200 | −103 | 40 | Linear |
| B | 4/25 | 117,600 | −103 | 57 | Linear |
| D | 96/25 | 25,000 | −104 | 40 | Linear |

The invention claimed is:

1. A siloxane monomer mixture obtainable by way of a process comprising the steps of
   a) ring opening polymerization of a cyclic monomer of the structure

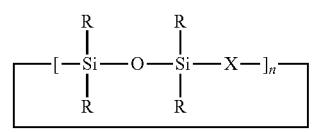

where X is selected from
   (i) a linear or branched alkylene group having from 1 to 14 carbon atoms; and
   (ii) an aromatic group having from 6 to 20 carbon atoms; each R is the same or different and is selected from H, OH, a hydrocarbon group having from 1 to 18 carbon atoms, a substituted hydrocarbon group having from 1 to 18 carbon atoms or a hydrocarbonoxy group having up to 18 carbon atoms and n is an integer between 1 and 6, in the presence of an acidic or basic ring opening polymerisation catalyst to form a mixture of siloxane monomers and linear oligomers, the linear oligomers comprising macrosiloxanes having a molecular weight ranging from 20,000 to 45,000 g/mol;
b) removing the linear oligomers prepared in step (a) optionally using a suitable solvent; and
c) removing the solvent, when present.

2. A siloxane monomer mixture obtainable in accordance with claim 1 wherein the cyclic monomer was 1,1,3,3,5,5,7,7-octamethyl-2,6-dioxa-1,3,5,7-tetrasilacyclooctane.

3. A siloxane monomer mixture obtainable in accordance with claim 1 wherein the ring opening catalyst is selected from the group of a heteropoly acid, perchloric acid, sulfuric acid, hydrochloric acid, HI, HBr, HClO$_4$, H$_2$SO$_4$, HNO$_3$, H$_3$PO$_4$, para-toluenesulfonic acid, trifluoroacetic acid, a perfluoroalkenesulfonic acid, methyl tosylate, methyl triflate and silyl ester trifluoromethane sulfonic acid.

4. A siloxane monomer mixture obtainable in accordance with claim 3 wherein
the ring opening catalyst is triflic acid.

5. A siloxane monomer mixture obtainable in accordance with claim 1 wherein step (a) is carried out at a temperature between 15° C. and 50° C.

6. A siloxane monomer mixture obtainable in accordance with claim 1 wherein when R is a substituted hydrocarbon group having from 1 to 18 carbon atoms, substituents are selected from halogen atoms; halogen atom containing groups; oxygen atoms; oxygen atom containing groups; nitrogen atoms; nitrogen atom containing groups; sulphur atoms; and sulphur atom containing groups.

7. A siloxane monomer mixture obtainable in accordance with claim 6 wherein when R is a substituted hydrocarbon group having from 1 to 18 carbon atoms, the halogen atom containing groups are selected from one or more of chloromethyl, perfluorobutyl, trifluoroethyl, and nonafluorohexyl and the oxygen atom containing groups are selected from one or more of (meth)acrylic, carboxyl and polyethers.

8. A method for obtaining a siloxane monomer mixture comprising the steps of
a) ring opening polymerization of a cyclic monomer of the structure

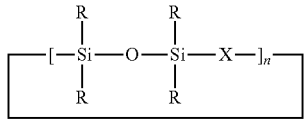

where X is selected from
(i) a linear or branched alkylene group having from 1 to 14 carbon atoms and which optionally may contain substituted groups; and
(ii) an aromatic group having from 6 to 20 carbon atoms; each R is the same or different and is selected from H, OH, a hydrocarbon group having from 1 to 18 carbon atoms, a substituted hydrocarbon group having from 1 to 18 carbon atoms or a hydrocarbonoxy group having up to 18 carbon atoms and n is an integer between 1 and 6, in the presence of an acidic or basic ring opening polymerisation catalyst to form a mixture of siloxane monomers and linear oligomers, the linear oligomers comprising macrosiloxanes having a molecular weight ranging from 20,000 to 45,000 g/mol;
b) removing the linear oligomers prepared in step (a) optionally using a suitable solvent; and
c) removing the solvent, when present.

9. A method in accordance with claim 8 wherein the cyclic monomer was 1,1,3,3,5,5,7,7-octamethyl-2,6-dioxa-1,3,5,7-tetrasilacyclooctane.

10. A method in accordance with claim 8 wherein the ring opening catalyst is selected from the group of a heteropoly acid, perchloric acid, sulfuric acid, hydrochloric acid, HI, HBr, HClO$_4$, H$_2$SO$_4$, HNO$_3$, H$_3$PO$_4$, para-toluenesulfonic acid, trifluoroacetic acid, a perfluoroalkenesulfonic acid, methyl tosylate, methyl triflate and silyl ester trifluoromethane sulfonic acid.

11. A method in accordance with claim 10 wherein the ring opening catalyst is triflic acid.

12. A method in accordance with claim 8 wherein step (a) is carried out at a temperature between 15° C. and 50° C.

13. A siloxane monomer mixture obtainable in accordance with claim 8 wherein when R is a substituted hydrocarbon group having from 1 to 18 carbon atoms, substituents are selected from halogen atoms; halogen atom containing groups; oxygen atoms; oxygen atom containing groups; nitrogen atoms; nitrogen atom containing groups; sulphur atoms; and sulphur atom containing groups.

14. A siloxane monomer mixture obtainable in accordance with claim 13 wherein when R is a substituted hydrocarbon group having from 1 to 18 carbon atoms, the halogen atom containing groups are selected from one or more of chloromethyl, perfluorobutyl, trifluoroethyl, and nonafluorohexyl and the oxygen atom containing groups are selected from one or more of (meth)acrylic, carboxyl and polyethers.

15. A process for obtaining a high molecular weight polysilalkylenesiloxane polymer comprising the following repeating units

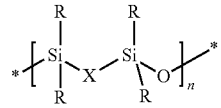

the process comprising
a) ring opening polymerization of a cyclic monomer of the structure

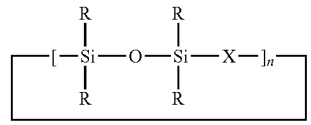

in the presence of an acidic or basic ring opening polymerisation catalyst;
where X is selected from
(i) a linear or branched alkylene group having from 1 to 14 carbon atoms and which optionally may contain substituted groups; and
(ii) an aromatic group having from 6 to 20 carbon atoms; each R is the same or different and is selected from H, OH, a hydrocarbon group having from 1 to 18 carbon atoms, a substituted hydrocarbon group having from 1 to 18 carbon atoms or a hydrocarbonoxy group having up to 18 carbon atoms and n is an integer between 1 and 6, in the presence of an acidic or basic ring opening polymerisation catalyst to form a mixture of siloxane monomers and linear oligomers, the linear oligomers comprising macrosiloxanes having a molecular weight ranging from 20,000 to 45,000 g/mol, b) removing the linear oligomers prepared in step (a) optionally using a suitable solvent; and c) removing the solvent, when present, to prepare the siloxane monomer mixture; then d) ring opening polymerizing the siloxane monomer mixture, in the presence of the acidic or basic ring opening polymerisation catalyst, at a temperature within the melting point range of the siloxane monomer mixture.

16. A process in accordance with claim 15 wherein the cyclic monomer was 1,1,3,3,5,5,7,7-octamethyl-2,6-dioxa-1,3,5,7-tetrasilacyclooctane.

17. A process in accordance with claim 15 wherein the ring opening catalyst is selected from the group of a heteropoly acid, perchloric acid, sulfuric acid, hydrochloric acid, HI, HBr, $HClO_4$, $H_2SO_4$, $HNO_3$, $H_3PO_4$, para-toluenesulfonic acid, trifluoroacetic acid, a perfluoroalkenesulfonic acid, methyl tosylate, methyl triflate and silyl ester trifluoromethane sulfonic acid.

18. A process in accordance with claim 17 wherein the ring opening catalyst is triflic acid.

19. A method in accordance with claim 15 wherein step (a) is carried out at a temperature between 15° C. and 50° C.

* * * * *